United States Patent [19]

Nieuwkerk et al.

[11] Patent Number: 5,438,128
[45] Date of Patent: Aug. 1, 1995

[54] METHOD FOR RAPID PURIFICTION OF NUCLEIC ACIDS USING LAYERED ION-EXCHANGE MEMBRANES

[75] Inventors: Yolanda Nieuwkerk, La Jolla, Calif.; Robert J. Barry, Kittery, Me.; Malcolm G. Pluskal, Acton; Richard A. Hamilton, Beverly, both of Mass.

[73] Assignee: Millipore Corporatin, Bedford, Mass.

[21] Appl. No.: 832,284

[22] Filed: Feb. 7, 1992

[51] Int. Cl.$^6$ .......................... C07H 1/06; C07H 1/08
[52] U.S. Cl. ................. 536/25.4; 536/25.41; 435/270
[58] Field of Search ............ 435/6, 270; 536/27, 536/28, 29, 25.4, 25.41

[56] References Cited

U.S. PATENT DOCUMENTS

| | | | |
|---|---|---|---|
| 4,895,806 | 1/1990 | Le et al. | 435/288 |
| 4,923,978 | 5/1990 | McCormick | 536/25.4 |
| 4,935,142 | 6/1990 | Sternberg | 210/634 |
| 4,935,342 | 6/1990 | Seligson et al. | 435/6 |
| 4,997,932 | 3/1991 | Reardon et al. | 536/25.4 |

FOREIGN PATENT DOCUMENTS 3717211  12/1988  Germany .

OTHER PUBLICATIONS

Hamilton et al., Abstract from ASBMB/Biophysical Society, Feb. 11, 1992, Product Brochure, The Nest Group, Inc.
Reddy et al., *Analt. Biochem.*, 168:324–331 (1988).
Helms et al., *DNA* 4:39–49 (1985).
Merion and Warren, *BioTechniques,* 7:60–67 (1989).

*Primary Examiner*—Douglas W. Robinson
*Assistant Examiner*—James O. Wilson
*Attorney, Agent, or Firm*—Hamilton, Brook, Smith & Reynolds

[57] ABSTRACT

The present invention relates to a device method and kit for the convenient and rapid isolation and purification of nucleic acids, proteins, peptides, carbohydrates and oligosaccharides from heterogeneous biological samples. The device comprises a membrane assembly comprised of layers of microporous, polymeric membranes functionalized with ion-exchange groups. The device is reusable for like samples, relatively inexpensive compared to currently available separation techniques and is disposable, thereby avoiding cross-contamination of biological samples.

9 Claims, 5 Drawing Sheets

METHOD FOR RAPID PURIFICTION OF NUCLEIC ACIDS USING LAYERED ION-EXCHANGE MEMBRANES

BACKGROUND OF THE INVENTION

Processing of nucleic acids for further studies, including sequencing, hybridization or PCR (polymerase chain reaction), will require isolation and purification of the plasmid DNA from chromosomal DNA, RNA, proteins and other contaminants present in bacterial cells. Most of these manipulations will require highly purified plasmid DNA.

A number of plasmid purification methods have been developed over the years. These methods include organic solvent extraction, separation according to buoyant density, size exclusion chromatography, and ion-exchange chromatography.

Alkaline lysis/organic solvent extraction has been the classic method to obtain purified plasmid DNA. The procedure involves numerous extraction and precipitation steps using organic solvents such as chloroform or phenol. Although an excellent method for obtaining significant quantities of highly purified plasmid DNA, it has serious drawbacks. The procedure is tedious and lengthy. There is often organic solvent contamination in the final product that must be removed before further studies. The procedure also has significant safety concerns due to the use of noxious chemicals in the process.

Separation according to buoyant density is another popular method of plasmid purification and provides high purity DNA. This method involves mixing a crude preparation containing the plasmid DNA with ethidium bromide dye and then over-layering the sample on top of a cesium chloride (CsCl) solution of higher buoyant density. This mixture is centrifuged at high speed to form a gradient of CsCl of increasing buoyant density. Macromolecules in the sample separate according to their buoyant density in the CsCl gradient, and a discreet band of plasmid DNA can be isolated from other contaminants, such as bacterial DNA. RNA is collected on the bottom of the tube as a pellet. However, this procedure is extremely time consuming, involving often 24 to 48 hours of centrifugation for a single sample, in order to form the CsCl gradient. Furthermore, the resulting band of isolated plasmid DNA is contaminated with ethidium bromide and residual CsCl and must be subjected to multiple organic washes prior to use.

Chromatographic procedures are also typical methods for purifying plasmid DNA. These methods include size exclusion chromatography, where separation is based on the size and solution conformation differences between linear and circular DNA, and ion-exchange chromatography, where separation is based on charge density differences between nucleic acids and other contaminating macromolecules.

Ion-exchange protocols have gained widespread acceptance as the method of choice for rapid isolation and purification of plasmid DNA. Using an appropriate buffer system, the anionic plasmid DNA is adsorbed to an ion-exchange support matrix which has been functionalized with anion exchange groups that bear a net positive charge under the buffer conditions used. The bound DNA can then be released from the ion-exchange surface by increasing the concentration of a suitable counter-ion, e.g., chloride ($Cl^-$). Variations on anionic exchange separations are described, for example, in U.S. Pat. No. 4,997,932 (porous beads with an anion-exchange surface for purifying nucleic acid); U.S. Pat. No. 4,935,342 (anion-exchange column); Warren and Merion, *BioChrom.* 3:118-126 (1988) (purification of synthetic oligonucleotides by anion-exchange high performance liquid chromatography using DEAE resin columns).

SUMMARY OF THE INVENTION

The present invention relates to a device for the convenient and rapid isolation and purification of nucleic acids, proteins, peptides, carbohydrates and oligosaccharides and other biological molecules available to ion-exchange from heterogeneous biological samples. The device comprises a membrane assembly comprised of layers of microporous, polymeric membranes functionalized with ion-exchange groups. In preferred embodiments, the device is adapted for use with a syringe or centrifuge. The device is suitably designed for purification of microgram quantities in good yield and high level of purity. The device is reusable for like samples, is relatively inexpensive compared to currently available separation techniques and is disposable, thereby avoiding cross-contamination of biological samples.

The present invention also relates to a method for isolation and purification of nucleic acids such as DNA and RNA from heterogeneous biological samples. It further relates to the rapid isolation and purification of plasmids from crude cell lysates resulting in high yields of bioreactive DNA suitable for further manipulation with a minimum of preparation. Proteins, peptides, carbohydrates and oligosaccharides can also be purified from heterogeneous biological samples according to the methods of the present invention.

The present invention further relates, but is not limited to, a kit comprised of a device housing a multilayer, microporous ion exchange membrane assembly and premeasured volumes of liquid or powdered reagents suitable for use with biological samples containing nucleic acids, proteins, peptides, or other bioactive molecules.

DETAILED DESCRIPTION OF THE INVENTION

Figure 1A:
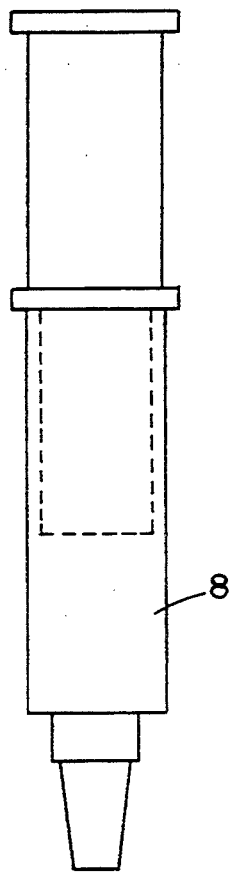
FIG. 1A is a schematic cross-sectional view of an ion-exchange device adapted for attachment to a syringe.
Figure 1A:
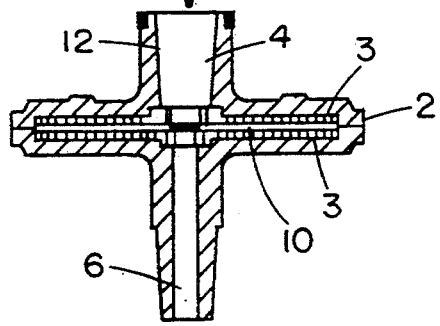

The device and method of the present invention are intended for use with a wide range of biological specimens, including, but not limited to, human bodily fluids and tissues, blood, urine, saliva, sperm, cell suspensions, bacterial cultures and virus particles, cells infected with viruses, tissue cultures and cell lines. The test sample may be prepared by known procedures, such as those used for lysing cells and/or viruses to obtain the nucleic acids. A standard methodology for lysis of cells is by alkaline extraction. Birnboim and Doly, *Nucleic Acids Research*, 1523-1523 (1979) and Molecular Cloning—A Laboratory Manual, 2nd Edition, Sanbrook et al. (Eds.), Cold Spring Harbor Laboratory Press (1989).

In order that the invention may be better understood, specific embodiments of devices for rapid isolation and purification of biomolecules will now be described in more detail with reference to the accompanying drawings. The foregoing and other objects, features and advantages of the invention will be apparent from the following more particular description of the preferred embodiments of the drawings in which like reference characters refer to the same parts throughout the different views. The drawings are not necessarily to scale, emphasis instead being placed upon illustrating the principles of the invention.

Figure 1B:
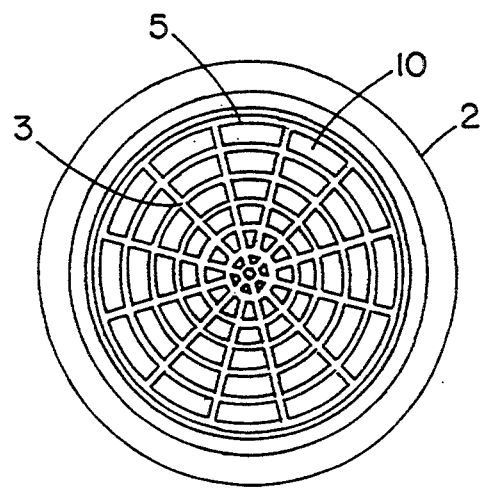
FIG. 1B is a plan view of the internal channelled surface of the housing shown in FIG. 1A.

FIG. 1A shows a device comprised of a circular housing 2 having an inlet 4 for sample delivery and an outlet 6 for sample collection. The device can be attached to a syringe 8 containing the sample to be purified by a connector 12, such as a female Luer-Lok TM. Located within the housing 2 is the membrane assembly 10 comprised of a plurality of multiporous membranes functionalized with ion-exchange groups. The internal surface of the housing is shown in FIG. 1B. Radial 3 and circumferential 5 channels contact the stacked membrane assembly 10 and provide support thereto and permit uniform flow of sample fluid over the membrane assembly.

Membranes used in the present invention should have a pore size (e.g., 0.1 to 12 microns) which facilitates high flow rate of sample under minimal pressure. The number of membranes stacked within the device should be restricted such that significant external mechanical force is not required to draw the sample through the device. The preferred number of membranes is from about one to about 20 layers, and preferably from one to about 10. The term "significant external mechanical force" is intended to mean a force which would require high pressure (e.g., high pressure liquid chromatography (HPLC)) to draw the sample through the membranes. One advantage of the present devices is that minimal backpressure is produced, thus, sample can freely flow through the membrane(s) with minimal positive or negative pressure. Although significant external pressure is not required, it should be understood that external pressure (i.e., centrifugal force, peristaltic pumps, HPLC or FPLC systems) may be used as a matter of experimental design or investigator choice.

The membrane (described in further detail below) is functionalized with ion-exchange groups capable of binding positively or negatively charged substances. By choosing an appropriate ion-exchange group and compatible buffering solutions, selected substances contained in a heterogeneous specimen can be isolated and purified by being adsorbed by the support, followed by desorption with a suitable counter-ion.

Sample fluid enters the inlet 4 and is directed toward the membrane assembly 10. Flow of sample into the membrane assembly 10 may be facilitated by positive pressure, such as that generated when pushing on the plunger of a syringe 8 attached to the inlet 4. Alternately, sample flow may be facilitated by negative pressure such as attaching the outlet 6 to a vacuum source which draws the sample through the membrane assembly 10.

As the sample flows through the device, under appropriate conditions, the substance of interest is retained by adsorption to the ion-exchange surface. By adjusting the conditions for purification, the majority of contaminating substances will not be retained by the membrane, or will be adsorbed so loosely that they are easily displaced by additional sample buffer or by small increases in the counter-ion concentration insufficient to desorb the biomolecules of interest. After the contaminating substances are washed through the device, the retained material is released from the membrane by increasing the counter-ion concentration. The optimal adsorption and desorption conditions for a desired substance can be readily determined with a minimum of experimentation by one of ordinary skill in the art.

Figure 2A:
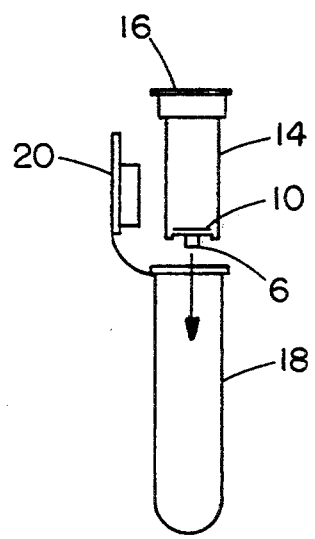
FIGS. 2A and 2B are schematic cross-sectional views of two ion-exchange cup device embodiments adapted for use in a centrifuge.
Figure 2B:
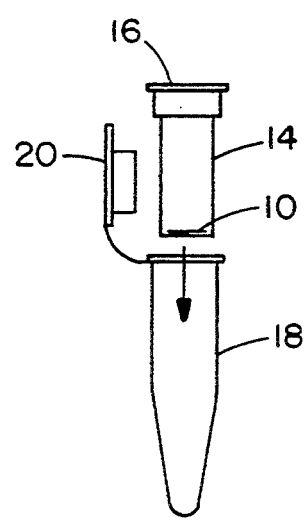

In another preferred embodiment of the present invention, shown in FIGS. 2A and 2B, the device comprises a small, cylindrical cup 14 with an opening at the top 16 to receive sample fluid, and the bottom embracing the membrane assembly 10 with outlet 6. Sample cup 14 is placed in a collecting vessel 18 having an insertable cap 20 hinged to the upper open end of the collection vessel 18 and insertable in the top 16 of the cup 14. As shown in FIG. 2B, the collecting vessel 18 is suitable for use in an ultracentrifuge. Under operating conditions, the sample cup 14 is filled with sample fluid and the cup 14/collecting vessel 18 combination, in closed position, can be placed into a centrifuge and subjected to centrifugal force sufficient to draw the sample fluid through the membrane assembly 10 into the collecting vessel 18. The initial filtrate containing contaminants is discarded, and the membrane is washed with an appropriate rinsing solution. This filtrate is also drawn through the membrane assembly 10 by centrifugal force, collected and discarded. The desired substance is then released from the membrane with appropriate elution buffer containing a high concentration of counter-ions.

Figure 3:
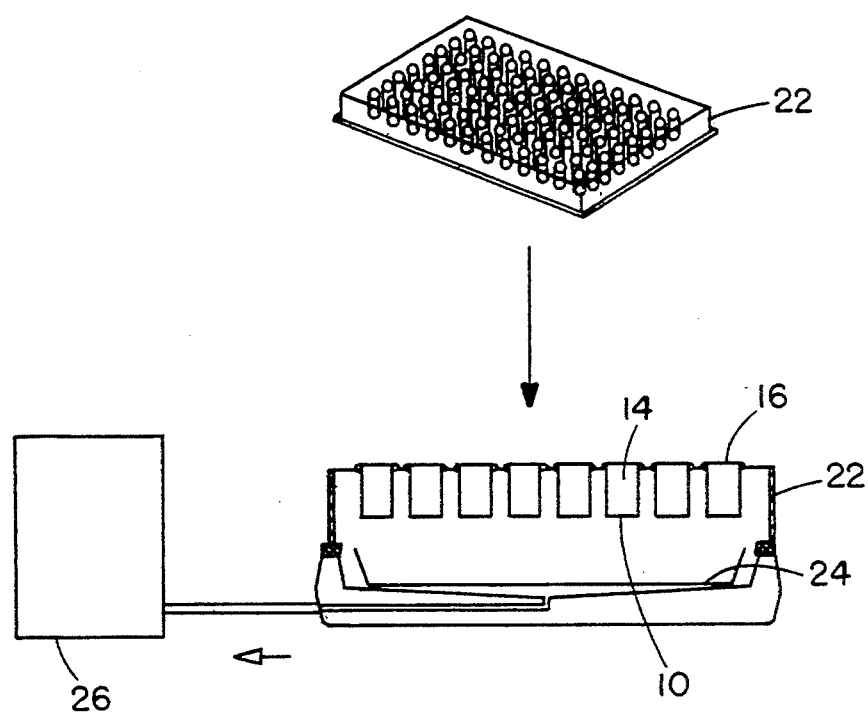
FIG. 3 is a schematic cross-sectional view of a multiwell ion-exchange device for receiving a multiplicity of sample preparations.

In another preferred embodiment, shown in FIG. 3, for use with small volumes of test fluid, the sample cups 14, as described above, are miniaturized and connected in a multi-well plate-like format 22. Each of the sample cups 14 comprise an inlet 16 for receiving sample and a bottom embracing the membrane assembly 10. The multi-sample cup plate 22 fits within a multi-well collection vessel 24, to which a vacuum source 26 may be applied. Sample fluids are added to the sample cups 14, vacuum is applied, and the sample is drawn through the membrane assembly 10. Contaminating substances are washed through the membrane assembly 10 with appropriate wash buffer and discarded. The desired substance is then released from the membrane using an appropriate elution buffer as described above, and collected in the multi-well collection vessel 24. This embodiment is particularly well-suited for selecting clones of interest.

Figure 4:
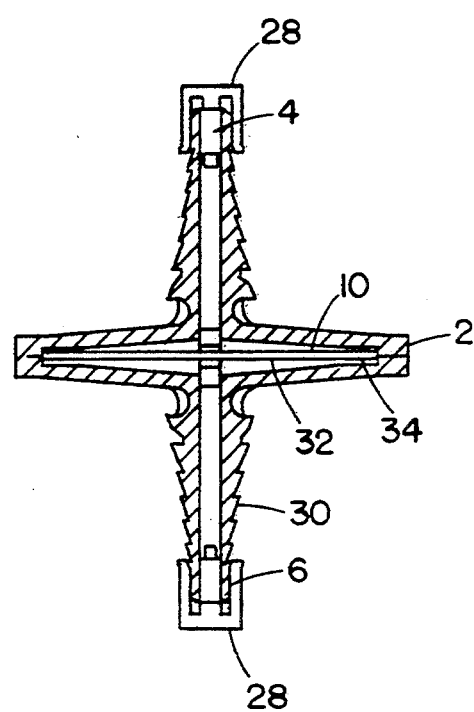
FIG. 4 is a schematic cross-sectional view of an ion-exchange device for large scale separations.

In yet another embodiment of the present invention, shown in FIG. 4, the device may be enlarged to accommodate large volumes of sample fluid. The device comprises a circular housing 2 having an inlet 4 and an outlet 6, each being fitted with a removable protective cap 28 to maintain moist state of membrane during storage. Within the circular housing 2 resides a membrane assembly 10 comprising a plurality of multiporous membranes that have been functionalized with ion-exchange groups layered with a filter support 32. The membrane assembly 10 is attached to the circular housing 2 by gaskets 34. A vacuum source is connected to the outlet 28, the hose adapter 30, and sample fluid, wash buffer, and elution buffer is drawn through the membrane assembly 10 as previously described in a preferred embodiment.

Figure 5:
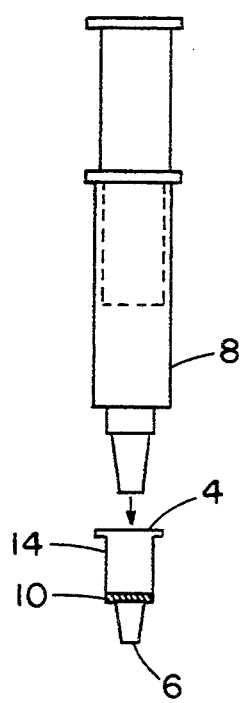
FIG. 5 is a schematic cross-sectional view of a minaturized ion-exchange device that has been adapted for attachment onto the end of a syringe or other liquid delivery system.

FIG. 5 illustrates another embodiment of the device which has been adapted for attachment to a syringe 8 or chromatographic column. The membrane assembly 10 is positioned within a miniaturized sample cup 14 which has an inlet 4 that is capable of receiving a syringe 8. The miniaturized size of the device permits separation of nanogram to microgram samples.

The ion-exchange membranes contained within the device of this invention are critical to achieving highly pure products. Functionalized groups attached to the membrane can be either weak or strong cationic (negatively charged) or anionic (positively charged) exchangers. A number of well known anionic and cationic surface chemistries can be exploited to functionalize porous membrane materials suitable for use with this invention. Among the anionic chemistries, diethylaminoethyl (DEAE; weak) functionalized cellulose membrane is preferred for nucleic acid purification. Other anionic chemistries include, but are not limited to, quaternary methyl amine (QMA; strong) and phosphate (strong). Cationic groups that can be used included but are not limited to carboxymethyl (CM; weak) and sulfylpropyl (SP; strong). The membrane or solid support itself can be selected from the following microporous membrane materials such as, but not limited to, cellulose, nylon, polyvinylidene fluoride (PVDF), polypropylene or other porous material, provided that the porosity of the material adequately permits sample to flow through the membrane without significant external mechanical force. The membrane material should also, when derivatized, have an adequate number of ion-exchange groups on its surface to selectively adsorb the biomolecules of interest without significant product loss.

The microporous membranes of the present invention are especially advantageous because the high surface area is readily accessible to bind the desired biomolecules within the confines of a small, easy-to-use, disposable device. As such, use of the device should require less volume of expensive matrix than conventional ion-exchange chromatography performed in columns, where the column must be of sufficient length to ensure adequate absorption of the sample. The membranes further provide adequate binding capacity to bind nucleic acids under conditions which allow undesired molecules (i.e., proteins, RNA) to flow through.

In a preferred embodiment, the devices of this invention will house a plurality of DEAE-derivatized cellulose membranes, i.e., from about one to about 20 membranes, stacked one on top of the other to form a column having a short bed depth. The preferred configuration of each membrane is circular or disc-shaped which are then placed within the housing in stacked or spiral configuration. Large open pores within the membrane (e.g., 12,000 Å diameter) allow free passage of large biological molecules through the membrane at high flow rates. The number of membranes stacked within the device should provide a short bed length to allow the device to be used with low pressure systems, such as a simple vacuum manifold or hand held syringe. The short bed depth reduces the quantity of eluant (e.g., 3–5 mls) required to elute the biomolecules of interest in a more concentrated form compared to traditional ion-exchange chromatography. The quantity of eluant used, however, will vary depending upon the sample used and the configuration of the device selected.

DEAE-derivatized membranes used in devices of this invention are physically and chemically stable to a wide range of solutions (pH 2–12), including but not limited to, urea, guanidine hydrochloride, ethylene glycol and detergents (e.g., non-ionic, cationic or zwitterionic). Anionic detergents, however, should be avoided as they may bind to the DEAE-derivatized membrane. Compatible organic solvents that may be used include, but are not limited to, 50% methanol, 20% ethanol, 20% propanol, 20% butanol, 8M urea, 8M guanidine hydrochloride, 50% ethylene glycol, 50% glycerol, 10% trifluoroacetic acid, 30% acetonitrile and 50% dimethylsulfoxide. These percentages represent known tolerable levels, however, higher titer solutions may be acceptable without compromising membrane integrity.

The above-described devices containing the ion-exchange membranes can be used to separate and purify nucleic acids, such as single-stranded DNA, double-stranded DNA, genomic DNA, phage lambda DNA, plasmid DNA and RNA, as well as proteins, peptides, carbohydrates and oligosaccharides from heterogeneous biological samples. For effective binding of the desired substance to the membrane, the substance itself must be in an optimally ionized configuration. The net charge of the substance, determining whether it will bind to a cationic or anionic exchanger depends on the nature of ionic groups on the molecules surface exposed to solvent and the pH and ionic strength of the buffer with which it is in equilibrium. Depending upon the identity of the sample and with a minimum of experimentation, it is possible to determine the buffer of choice for maximum binding of the desired substance to the membrane. For nucleic acid samples, the buffer of choice would be from about 20–100 mM (20 mM preferred) Tris HCl with from about 0M to about 1M salt (NaCl). For separation and purification of protein and peptide samples, it is desirable to use from about 20 mM Tris HCl with from 10 mM to about 0.5M salt (pH 4–10).

According to the method of the invention, sample containing the desired substance is first diluted, reconstituted or resolubilized in the buffer of choice. The sample fluid is then introduced into an equilibrated device through the inlet opening and permitted to flow through the membrane assembly using minimal positive or negative pressure. The flow rate of the test fluid through the membrane may be rapid due to the large surface area available to bind the desired substance, but may be increased by regulating the pressure exerted on the device. Binding of the desired substance takes place almost instantaneously, and remains intact until released with the proper elution buffer containing an increased concentration of the appropriate counter-ion.

After the desired substance is retained by the membrane assembly, a second buffer is washed through the membrane assembly to selectively remove contaminants from the membrane. This wash buffer will typically be of a higher ionic strength than the binding buffer, yet not of sufficient ionic strength to elute the desired substance.

The elution buffer is typically of a higher ionic strength than the wash buffer. Optimal pH and salt concentration of the eluting buffer can be easily determined with a minimum of experimentation. The elution buffer selectively releases the retained substance from the membrane. Consequently, when the desired substance is released or eluted from the membrane, it is contained in a buffer compatible with subsequent biological procedures. The desired substance will be essentially free from contaminants and sufficiently concentrated for further processing due to smaller buffer volumes required for the purification.

In a particularly preferred method, plasmid DNA can be isolated from a crude bacterial cell lysate, in a stepwise manner, by first removing biomolecules and cellular contaminant material that do not bind to the ion-exchange membrane(s), including proteins and RNA. Any residual RNA is then removed from the bound DNA during a subsequent wash step. The conditions of loading and elution can be modified such that the eluted RNA is essentially pure and free of RNA and protein contamination. In the final elution step, the purified plasmid DNA is released from the membrane and recovered for further experimental manipulation and/or characterization. Thus, the process yields purified DNA or usable RNA, which can subsequently be used for restriction enzyme digestion, cloning, ligation, sequencing or other applications requiring high purity DNA.

Depending upon the particular application, the device may be reused for multiple purifications of like sample by first flushing the device with an appropriate elution buffer having high salt concentration or low pH which is suitable for releasing tightly bound molecules on the membrane. Thereafter, the device should be re-equilibrated by washing the membrane with a buffer of low ionic strength, and preferably one which is essentially of neutral pH. If reuse of the device is not imminant, the device can be stored in an appropriate preservation solution, such as 10-20% (v/v) alcohol (e.g., ethanol or isopropanol) by itself, or in combination with an appropriate buffer (e.g., 20 mM Tris (pH 6.0-9.0), 0.1-0.5M NaCl and 1-100 mM EDTA). A particularly preferrred equilibration buffer will contain 0.4M NaCl, 20 mM Tris (pH 7.0), 10 mM EDTA (pH 8.0) and 15% isopropanol. Other storage solutions which preserve the ion-exchange membrane can be determined by routine experimentation. Equilibration, as discussed above, is necessary to remove the preservation solution prior to use.

The ion-exchange device, after multiple use, can be regenerated by successive washings with water, acid (e.g., 0.5N HCl) and base (e.g., 0.5N NaOH). As discussed above, the regenerated device can be stored in preservative solution for later use.

The invention is further directed to kits for purification and isolation of biomolecules. The kit will comprise a device having a plurality of ion-exhange membranes and a plurality of buffer solutions of varying ionic strength to adsorb and then release sample of interest from the membrane. A particularly preferred kit will comprise a DEAE derivatized membrane (e.g., cellulose) and reagents for nucleic acid purification. More particularly, the kit will comprise an equilibration buffer (as described in detail above), a wash buffer and an elution buffer. For plasmid purification, a preferred wash buffer will comprise: 400 mM NaCl, 20 mM Tris (pH 7.0), 10 mM EDTA (pH 8.0) and 15% isopropanol; and the elution buffer will comprise: 0.6M-4M NaCl (2.0M preferred), 20 mM Tris (pH 7.0), 20 mM EDTA (pH 8.0) and 15% isopropanol. It should be recognized, however, that modification and optimization of these buffers can be ascertained by the investigator without undue experimentation and will depend upon sample type, membrane choice, number of ion-exchange membranes in the device and identity of the ion-exchange used. The kit may optionally contain reagents for cell lysis.

There are a number of advantages using ion-exchange membranes for biomolecule separation that offer improvements to traditional ion-exchange column methodologies. The various configurations of the device of this invention permit the purification and recovery of small quantities of sample. For example, microliter quantities of sample can be conveniently recovered using the ultracentrifuge cup embodiment. This is particularly useful for further manipulation of the sample, such as by PCR. Further, the devices can be regenerated and reused multiple times for purification of like samples, but are designed to be disposable when different samples of interest are being investigated. The disposability aspect of the devices eliminate the possibility of cross contamination during the purification process.

The method of this invention is further illustrated by the following non-limiting examples:

EXAMPLE 1

PLASMID PURIFICATION

For preparation/growth of transformed cells, general methods outlined by Maniatis, "A Molecular Guide to Cloning", were followed. In general, 4 pellets from 500 ml cultures transformed with pBR322 were grown overnight in Luria-briani media with ampicillin (35-50 $\mu$g/ml) (LB amp) media. Bacterial pellets were obtained by subjecting the liquid cultures to slow speed centrifugation (i.e., 10 min. at 3000 rpm in Sorvall Gs 3 Rotor or equivalent).

Ten ml of 50 mM Tris, 10 mM EDTA (pH 8.0), containing 100 $\mu$g/ml RNAse A was added to each bacterial pellet from the 500 ml overnight culture. The buffer was swirled in the centrifuge tube to resuspend the pellets. To each tube was added 10 ml 0.2M NaOH, 1.0% SDS. This was mixed by swirling and incubated at room temperature for 5 minutes. After the 5 minute incubation was complete, 10 ml 2.55M potassium acetate (pH 5.2) was added to each pellet, again swirling to mix the components. This was centrifuged for 30 minutes in Sorvall SS34 rotor (12,000$\times$g) to obtain a clear supernatant free from cellular particulate and repeated to remove additional debris.

The supernatant generated in the above procedure was removed from the pellet promptly after centrifugation. After pooling all fractions, 20 ml was loaded directly on to the pre-equilibrated ion-exchange membrane device of the invention (FIG. 4) and a traditional ion-exhange column (Qiagen Q500, Qiagen, Inc., Studio City, Calif.) (after equilibration with Qiagen equilibration buffer as per protocol). Samples separated using Qiagen Q500 followed Qiagen protocol and used Qiagen buffers. The ion-exchange membrane device was loaded using a 30 ml syringe to push the crude prep through the device. Unbound and weakly binding impurities were washed from the device by pushing 20 ml of 20 mM Tris, 10 mM EDTA, 0.4 m NaCl, 15% isopropanol through the device. The plasmid DNA was eluted by pushing 15 ml of 20 mM Tris, 20 mM EDTA, 2.0M NaCl, 15% isopropanol through the device and collecting this eluant in a clean tube. Fifty microliters was removed from each fraction, mixed with loading dye and run on an agarose gel.

To remove salt from the purified plasmid DNA, one volume of isopropanol was added to the final elution buffer and was centrifuged for 15 min. at 4° C. The supernatant was poured off, the pellet was rinsed with 70% ethanol and then dried. The pellet was resuspended in a buffer of 10 mM Tris and 1 mM EDTA (pH 7.6) and samples were loaded on to an agarose gel.

The quantities of DNA eluted using this method ranged from 343 µg to 483 µg for the large size devices of this invention (capacity 100-500 µg), and 178 µg was eluted using the Qiagen Q500 ion-exhange column/kit (500 µg capacity) from plasmid preparations. On other occasions, separations on Qiagen Q500 yielded 500 µg DNA. Total purification time after sample preparation using the device of this invention ranged from 30 seconds to 5 minutes, whereas the Qiagen Q500 column took 15 minutes to 1 hour.

EXAMPLE 2

PLASMID PURIFICATION

For preparation/growth of transformed cells, general methods outlined by Maniatis were followed. Several 500 ml cultures transformed with pBR322 were grown overnight in LB media containing 35-50 µg/ml ampicillin. Bacterial pellets were obtained by subjecting the liquid cultures to slow speed centrifugation (i.e., 10 min. at 3000 rpm in Sorvall Gs 3 Rotor or equivalent).

Ten ml of 50 mM Tris, 10 mM EDTA (pH 8.0) containing

Ten ml of 50 mM Tris, 10 mM EDTA (pH 8.0) containing 100 µg/ml RNAse A was added to each bacterial pellet from 500 ml overnight culture. The buffer was swirled in the centrifuge tubes to resuspend the pellets. To each tube was added 10 ml 0.2M NaOH, 1.0% SDS. This was mixed by swirling to mix the components. This was centrifuged for 30 minutes in Sorvall SS34 rotor (12,000×g) to obtain a clear supernatant free from cellular particulate and repeated to remove additional debris.

The supernatant generated in the above procedure was removed from the pellet promptly after centrifugation. After pooling all fractions, 20 ml was loaded directly onto the pre-equilibrated ion-exchange membrane device of this invention (FIG. 4). The devices were equilibrated using 10 ml of 0.4M NaCl, 15% ethanol, 0.15% Triton X 100, and 50 mM Mops (pH 7.0). The ion-exchange membrane devices were loaded using a 30 ml syringe to push the crude prep through the device. Unbound and weakly bound impurities were washed from the device by pushing 10 ml of 0.4M NaCl, 15% ethanol, and 50 mM Mops (pH 7.0) through the device. The plasmid DNA was eluted by pushing 15 ml of 0.6M NaCl, 15% ethanol and 50 mM Mops (pH 7.0) through the device and collecting this eluant in a clean tube. 50 microliters was removed from each fraction, mixed with loading dye and run on an agarose gel.

To remove salt from the purified plasmid DNA, one volume of isopropanol was added to the final elution buffer and was centrifuged for 15 min. at 4° C. The supernatant was poured off, the pellet was rinsed with 70% ethanol and then dried. The pellet was resuspended in a buffer of 10 mM Tris and 1 mM EDTA (pH 7.6) and samples were loaded onto an agarose gel. A230-A300 scans of the final elution fraction show the 260 nm peak and the A260/A280 ratio and nucleic acid concentration was 1.76 using the device of this invention. Each fraction was run on an 0.8% agarose gel as follows: Lane 1=crude prep prior to purification; Lane 2=flow through lane; Lane 3=wash fraction lane; Lane 4=eluted pBR322 fraction.

In order to test the bioactivity of the DNA, the ethanol precipitated DNA was restriction enzyme digested and run on a 0.8% agarose gel as follows: Lane 0=pBR322 control; Lane 1=Hae ll digest; Lane 2=Hae III digest; Lane 3=Hind III digest; Lane 4=undigested; Lane 5=undigested and unprecipitated.

In conclusion, the pBR322 DNA eluted using this protocol was RNA free and protein free and was restriction enzyme digestible.

EXAMPLE 3

SEPARATION OF HUMAN TRANSFERRIN AND β-LACTOGLOBULIN A

The performance of a DEAE-derivatized cellulose ion-exchange membrane device of this invention (FIG. 4) was compared to the performance of MemSep TM 1000 DEAE (Millipore Corp., Bedford, Mass.) using a linear gradient followed by a step gradient. A 10 mg/ml mix of human transferrin and β-lactoglobulin A was used as the starting material for protein separations. Separations were performed on a Waters TM 650 HPLC system. A four buffer system was used and mixing was performed by the HPLC pump (Buffer A=100 mM Tris-HCl; Buffer B=100 mM Trizma Base; Buffer C=1.0M NaCl; Buffer D=deionized water). Injections of the 10 mg/ml mix ranged from 1-100 µl in various runs.

In both separations, 10 µl (10 µg) of the two protein mix was injected in each run. Table 1 shows the gradient setup used for both separations. The gradient formed was a curved linear gradient. The greater resolution in the resulted from the increased bed depth of the MemSep TM 1000 over the disposable device of the invention. However, the more rapid elution of protein peaks using the ion-exchange device of this invention resulted from the smaller bed depth of this device.

A step gradient was also used to separate the peaks of the same two protein mixture described above. The gradient parameters are shown in Table 2. Both sets of peaks elute in the same steps. However, the peaks from the present device, were again eluted sooner than the MemSep peaks generated using MemSep TM 1000. This is the result of the decreased depth of the present device as compared to the MemSep TM 1000 bed.

TABLE 1

| Time | Flow | % A | % B | % C | % D |
|---|---|---|---|---|---|
| Initial Conditions | 5.600 | 12 | 8 | 0 | 80 |
| 0.10 | 5.600 | 12 | 8 | 0 | 80 |
| 1.00 | 5.600 | 12 | 8 | 0 | 80 |
| 11.00 | 5.600 | 12 | 8 | 19 | 61 |
| 15.00 | 5.600 | 12 | 8 | 80 | 0 |
| 16.00 | 5.600 | 12 | 8 | 80 | 0 |
| 17.00 | 5.600 | 12 | 8 | 0 | 80 |
| 18.00 | 5.600 | 12 | 8 | 0 | 80 |
| 20.00 | 0.100 | 12 | 8 | 0 | 80 |

TABLE 2

| Solution | % A | % B | Volume |
|---|---|---|---|
| 1 | 0 | 80 | 4 ml |
| 2 | 4 | 76 | 4 ml |
| 3 | 12 | 68 | 4 ml |
| 4 | 80 | 0 | 4 ml |

EXAMPLE 4

SEPARATION PERFORMED ON MILLISEP USING A HAND HELD SYRINGE

The step gradient described in Example 3 was used to separate the two components of the protein mix using a hand held syringe rather than an expensive HPLC instrumentation.

The following conditions may be used to perform the syringe operated separation. Solutions prepared to contain relative proportion of buffer A and B as outlined in Table 1 above (Buffer A: 20 mM Tris pH 8.0; Buffer B: 20 mM Tris pH 8.0+1.0M NaCl) were used. A four milliliter injection was used in order to ensure maximum recovery of the protein peak.

Equivalents

Those skilled in the art will recognize, or be able to ascertain using not more than routine experimentation, many equivalents to the specific embodiments of the invention described herein. Such equivalents are intended to be encompassed by the following claims.

We claim:

1. A method for the rapid isolation and purification of a nucleic acid of interest from a cell lysate sample containing the nucleic acid of interest using ion-exchange membranes, comprising the steps of:

a) applying a buffered solution of sample containing nucleic acid to a membrane assembly which contains a plurality of stacked microporous membranes with pore sizes of 0.1 to 12 microns functionalized with ion-exchange groups capable of adsorbing ionized nucleic acids thereto, wherein the nucleic acid is retained by the membrane;

b) washing the membrane assembly with an elution buffer of a determined ionic strength sufficient to release weakly adsorbed elute contaminating substances contained in said sample from the membrane;

c) washing the membrane assembly with an elution buffer of determined ionic strength sufficient to release the bound nucleic acid from the membrane; and d) recovering the purified nucleic acid.

2. The method of claim 1 wherein the nucleic acid is selected from the group consisting of single-stranded DNA, double-stranded DNA, genomic DNA, phage lambda DNA, plasmid DNA, and RNA.

3. The method of claim 1 wherein the nucleic acid is plasmid DNA.

4. The method of claim 1 wherein the ion-exchange groups are anionic exchangers.

5. The method of claim 4 wherein the anionic exchangers are selected from the group consisting of diethylaminoethyl (DEAE), quaternary methyl amine, and phosphate.

6. The method of claim 1 wherein the membrane layers are cellulose, nylon, polyvinylidene fluoride or polypropylene.

7. The method of claim 1 wherein the membrane is a diethylaminoethyl (DEAE) functionalized cellulose membrane.

8. The method of claim 1, further comprising equilibrating the membrane assembly with a buffer of low ionic strength prior to step (a).

9. The method of claim 1 wherein the membrane assembly comprises from about 1 to about 20 membrane layers.

* * * * *